United States Patent
Sehgal et al.

(10) Patent No.: US 6,914,127 B2
(45) Date of Patent: Jul. 5, 2005

(54) ACELLULAR RED BLOOD CELL SUBSTITUTE

(75) Inventors: Lakshman R. Sehgal, Flossmoor, IL (US); Richard E. De Woskin, Mount Prospect, IL (US); Gerald S. Moss, Highland Park, IL (US); Steven A. Gould, Highland Park, IL (US); Arthur L. Rosen, Wilmette, IL (US); Hansa Sehgal, Flossmoor, IL (US)

(73) Assignee: Northfield Laboratories, Inc.

( * ) Notice: Subject to any disclaimer, the term of this patent is extended or adjusted under 35 U.S.C. 154(b) by 377 days.

(21) Appl. No.: 10/348,579

(22) Filed: Jan. 21, 2003

(65) Prior Publication Data

US 2003/0130487 A1 Jul. 10, 2003

Related U.S. Application Data

(63) Continuation of application No. 09/995,203, filed on Nov. 27, 2001, now Pat. No. 6,552,173, which is a continuation of application No. 09/638,471, filed on Aug. 14, 2000, now Pat. No. 6,323,320, which is a continuation of application No. 08/484,942, filed on Jun. 7, 1995, now Pat. No. 5,747,649, which is a continuation of application No. 08/031,563, filed on Mar. 15, 1993, now Pat. No. 6,133,425, which is a continuation of application No. 07/616,727, filed on Nov. 21, 1990, now Pat. No. 5,194,590, which is a continuation of application No. 07/315,130, filed on Feb. 23, 1989, now abandoned, which is a continuation of application No. 06/876,689, filed on Jun. 20, 1986, now Pat. No. 4,826,811.

(51) Int. Cl.[7] .................................................. A61K 37/14
(52) U.S. Cl. ........................ 530/385; 514/6; 514/832; 424/529
(58) Field of Search .............................. 530/385; 514/6, 514/832; 424/529

(56) References Cited

U.S. PATENT DOCUMENTS

| | | | | |
|---|---|---|---|---|
| 4,001,401 A | * | 1/1977 | Bonsen et al. | 424/177 |
| 4,826,811 A | * | 5/1989 | Sehgal et al. | 514/6 |
| 5,194,590 A | * | 3/1993 | Sehgal et al. | 530/385 |
| 5,464,814 A | * | 11/1995 | Sehgal et al. | 514/6 |
| 5,747,649 A | * | 5/1998 | Sehgal et al. | 530/385 |
| 6,133,425 A | * | 10/2000 | Sehgal et al. | 530/385 |
| 6,323,320 B1 | * | 11/2001 | Sehgal et al. | 530/385 |
| 6,552,173 B2 | * | 4/2003 | Sehgal et al. | 530/385 |

OTHER PUBLICATIONS

Sehgal et al., Transfusion, vol. 23(2), pp. 158–162, 1983.*
Sehgal et al., Surgery, vol. 95(4), pp. 433–438, 1984.*

* cited by examiner

*Primary Examiner*—C. Sayala
(74) *Attorney, Agent, or Firm*—McDonnell Boehnen Hulbert & Berghoff

(57) ABSTRACT

An acellular red blood cell substitute which comprises an essentially tetramer-free, substantially stroma-free, cross-linked, polymerized, pyridoxylated hemoglobin and a nontoxic, pharmaceutically acceptable carrier, its use and a process for preparing said acellular red blood cell substitute.

13 Claims, 10 Drawing Sheets

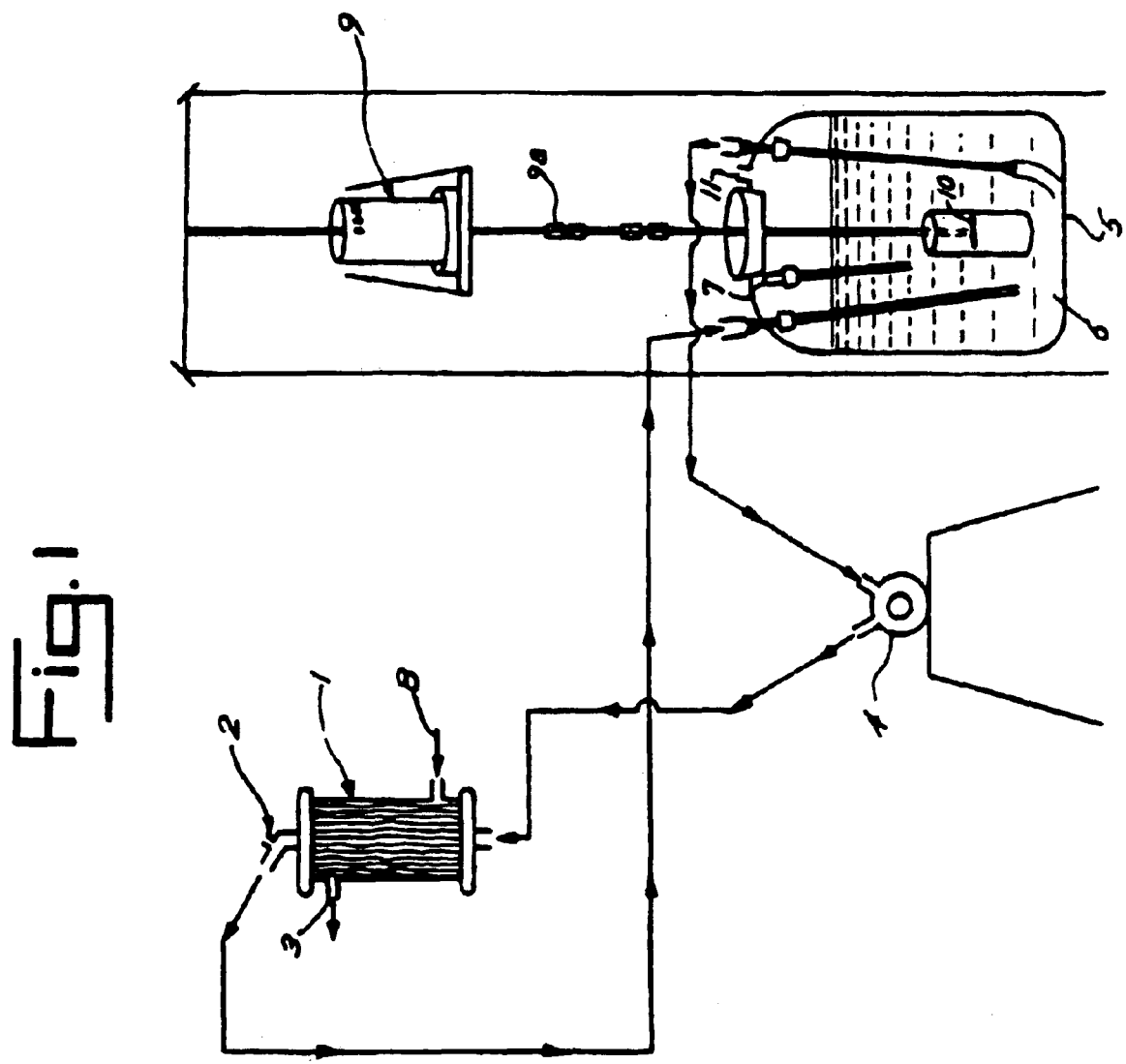

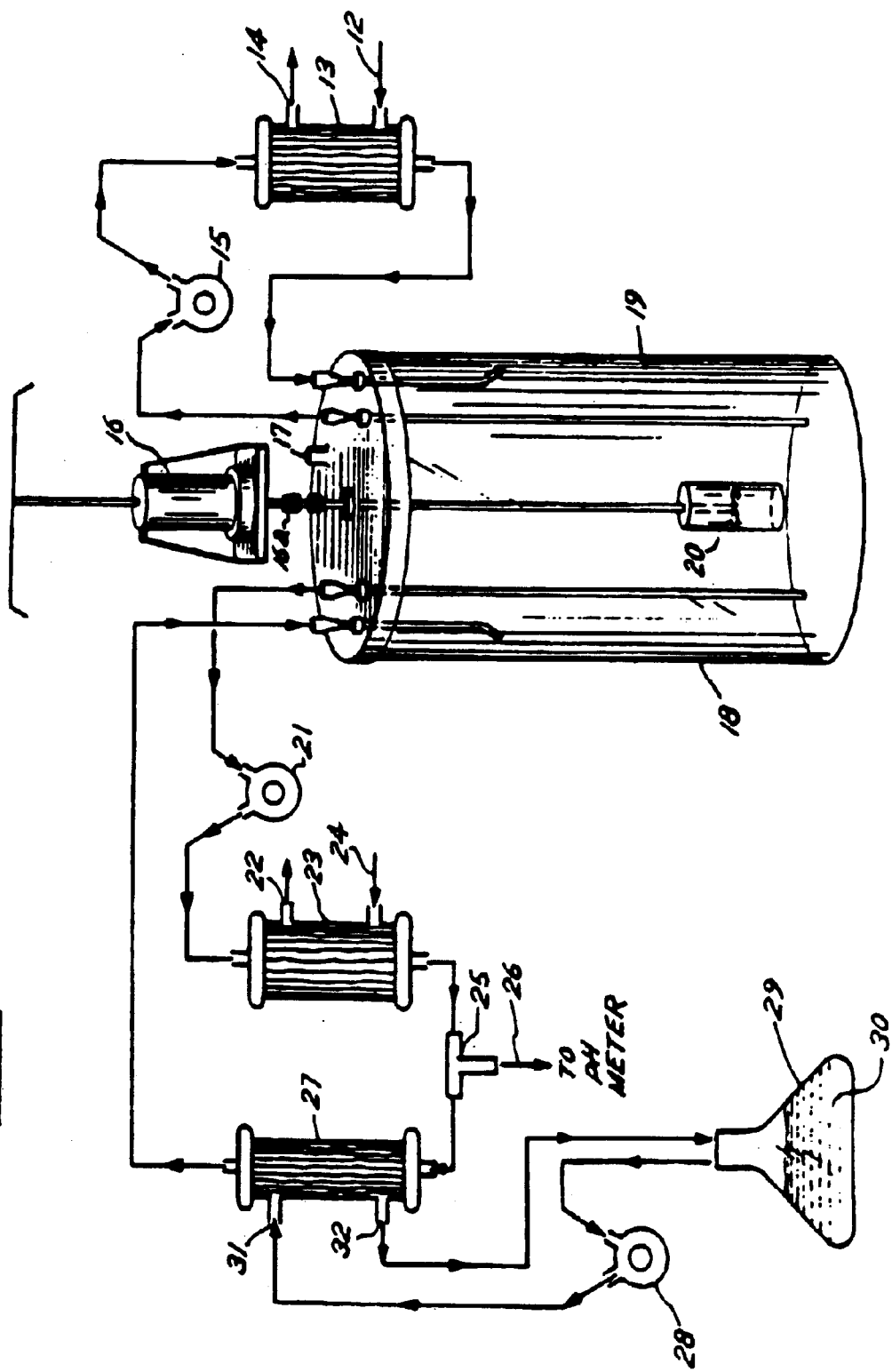

3 HOUR POLYMERIZATION

6 HOUR POLYMERIZATION

7 HOUR POLYMERIZATION

ACELLULAR RED BLOOD CELL SUBSTITUTE

This is a continuation of application Ser. No. 09/995,203, filed Nov. 27, 2001, now U.S. Pat. No. 6,552,173, which is a continuation of application Ser. No. 09/638,471, filed Aug. 14, 2000, now U.S. Pat. No. 6,323,320, which is a continuation of application Ser. No. 08/484,942, filed Jun. 7, 1995, now U.S. Pat. No. 5,747,649, which is a continuation of application Ser. No. 08/031,563, filed Mar. 15, 1993, now U.S. Pat. No. 6,133,425, which is a continuation of application Ser. No. 07/616,727, filed Nov. 21, 1990, now U.S. Pat. No. 5,194,590, which is a continuation of application Ser. No. 07/315,130, filed Feb. 23, 1989, now abandoned, which is a continuation of application Ser. No. 06/876,689, filed Jun. 20, 1986, now U.S. Pat. No. 4,826,811.

BACKGROUND OF THE INVENTION

1. Field of the Invention

This invention relates to an acellular red blood cell substitute comprising an essentially tetramer-free, cross-linked, polymerized, pyridoxylated hemoglobin solution which is free of stromal contaminants. It further relates to a method of preparing the acellular red blood cell substitute.

2. Description of Related Art

For several years, stroma-free hemoglobin has been known in the art to have oxygen transport and reversible oxygen (or ligand) binding capacities. Since toxicity problems have precluded use as a blood substitute, stroma-free hemoglobin has required further modifications to provide a nontoxic, useful pharmaceutical product. In U.S. Pat. Nos. 4,001,200; 4,001,401 and 4,053,590, a polymerized, cross-linked, stroma-free hemoglobin is disclosed as a blood substitute for carrying oxygen to tissues and organs and as a blood plasma expander. Pyridoxylating the stroma-free hemoglobin has been shown to favorably alter reversible oxygen binding capacities and increase the stability and shelf-life of the biological product. J. Surgical Research 30:14–20 (1981). Pyridoxylated hemogobin polymerized with glutaraldehyde has been described and characterized in L. R. Sehgal, et al. In Vitro and In Vivo Characteristics of Polymerized, Pyridoxylated Hemoglobin Solution, Fed. Proc. 39:2383 (1980); L. R. Sehgal, et al., Preparation and In Vitro Characteristics of Polymerized, Pyridoxylated Hemoglobin, Transfusion 23(2):158 (March–April 1983). Further, the ability of the polymerized, pyridoxylated hemoglobin to act as an oxygen carrier has been disclosed in L. R. Sehgal, et al., Polymerized, Pyridoxylated Hemoglobin: A Red Cell Substitute with Normal Oxygen Capacity, Surgery 95(4):433–38 (April 1984); L. R. Sehgal, et al., An Appraisal of Polymerized, Pyridoxylated Hemoglobin as an Acellular Oxygen Carrier, Advances in Blood Substitute Research 19–28 (Alan R. Liss, Inc. 1983).

For years investigators have reported that hemoglobin solutions prepared by various techniques, while capable of carrying sufficient quantities of oxygen to support life, have undesirable side effects. The most troubling side effect is a decrease in kidney performance. These changes were thought to be due to the presence of unwanted contaminants such as bacterial endotoxin or fragments of red cell membranes (stroma). While contaminants such as these can indeed produce renal alterations, hemoglobin solutions essentially free of the above contaminants still produce substantial renal dysfunction. Although this dysfunction is temporary and reversible, it can be very alarming in a clinical situation such as hemorrhagic shock, as the kidney is already at risk in this low blood flow state. The cause for the renal dysfunction has been ascribed to physiologically unacceptable amounts of unpolymerized hemoglobin tetramer. Other undesirable side effects of the infusion of tetrameric hemoglobin are renal toxicity, vasoconstriction, hemoglobinurea, depression of heart rate, elevation of mean arterial blood pressure and extra-vasation of infusate especially into the peritoneal cavity.

In practice, no known hemoglobin-derived blood substitute has been successful in totally avoiding toxicity problems These products prepared according to the state of the art have been found to contain varying amounts of hemoglobin tetramer. For example, the process of preparation according to U.S. Pat. Nos. 4,001,200; 4,001,401 and 4,053,590 does not provide a therapeutically useful product. First, like other proceses, there is an undesirable, high amount of unpolymerized hemoglobin tetramer in the final product. Secondly, too many contaminants such as toxic residual toluene may remain in the solution since they may not be completely removed during preparation. Thirdly, the product, described as having a $P_{50}$ of 100–120 mm Hg, would be nonfunctional physiologically in that the hemoglobin solution would not pick up oxygen in the lungs. Lastly, increased proportions of higher molecular weight polymers yield a product of high gelation lability such that subsequent steps of filtration and purification are difficult or impossible to accomplish except in unacceptably dilute solutions.

SUMMARY OF THE INVENTION

It is an important object of the present invention to provide a nontoxic hemoglobin solution therapeutically useful as an acellular red blood cell substitute.

Another object is to provide a nontoxic hemoglobin solution with reversible oxygen binding capacities that will not require compatibility studies with a recipient.

A further object is to provide a pure, polymeric hemoglobin solution essentially devoid of unmodified hemoglobin tetramer with normal oxygen carrying capacity.

A still further object is to provide a temporary oxygen carrier which can be rendered substantially free of microbial and viral antigens and pathogens.

With the foregoing and other objects in view, the invention herein provides an essentially tetramer-free, cross-linked, polymerized, pyridoxylated hemoglobin which is substantially free of stroma and other contaminants.

BRIEF DESCRIPTION OF THE DRAWINGS

Referring to the accompanying drawings, there are provided fourteen figures, to be hereinafter described in detail, illustrating this invention and its departure from the art wherein:

FIG. 1 is a schematic diagram of the batch method of pyridoxylation;

FIG. 2 is a schematic diagram of the membrane facilitated pyridoxylation and polymerization according to this invention;

DETAILED DESCRIPTION OF THE PREFERRED EMBODIMENT

Figure 3A:
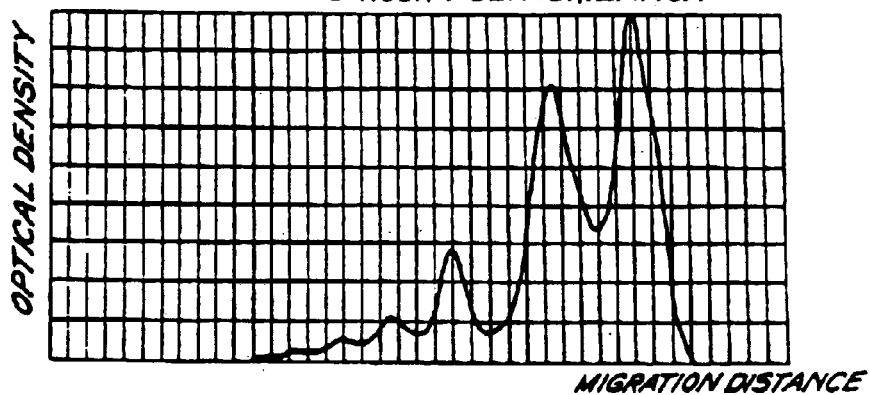
FIGS. 3A, 3B and 3C are graphs showing a densitometric scan of essentially tetramer-free, cross-linked, polymerized, pyridoxylated hemoglobin separated by SDS-polyacrylamide gel electrophoresis.

The present invention concerns an acellular red blood cell substitute comprising an essentially tetramer-free, cross-linked, polymerized, pyridoxylated hemoglobin which is substantially free of stroma and other contaminants.

For purposes of this invention, the term cross-linked means the chemical emplacement of molecular "bridges" onto or into a molecule, or between molecules with the purpose of altering the shape, size, function or physical characteristics of the molecule. The term essentially tetramer-free denotes the level of purity with respect to tetramer contamination at which certain biological responses to tetramer administered into a mammal are no longer present. A main criterion is the absence of alterations in renal function when pharmaceutically effective amounts are infused, that is, at a level of purity of about 98% or better (less than about 2% of tetramer is present). The "ultrapurified" or "purified" product have the same meaning as being essentially tetramer-free. The term polymerizing solution defines a solution containing a "cross-linking" or polymerizing agent, such as glutaraldehyde, imido esters, diaspirin or others, in a biochemically suitable carrier. The term semipermeable membrane connotes a membrane permeable to some molecular species and not to others and, in particular, a membrane which acts as a selective filter excluding molecular weights of about 30,000 daltons and above.

The product of the process according to the present invention, a polymerized, pyridoxylated hemoglobin solution essentially free of tetrameric (native) hemoglobin and various other contaminants, is physiologically acceptable as well as therapeutically and clinically useful. The product has reversible oxygen binding capacities which is necessary for oxygen transport properties. Most notably, the product demonstrates good loading and unloading characteristics in usage which correlates to having an oxygen-hemoglobin dissociation curve ($P_{50}$) similar to whole blood. The product shows a high affinity for binding oxygen in the capillaries through the lungs and then adequately releases oxygen to the tissues in the body. The product also does not require compatibility studies with the recipient.

The process of this invention is unique in that it yields a product free of tetramer contamination at a level heretofore unknown in the fractionation and purification of polymeric hemoglobins. The process of this invention provides a further advantage in that it can render the final product substantially free of microbial and viral antigens and pathogens. Such antigens and pathogens include, for example, bacterial, rickettsial, fungal, protozoan, viral and other organisms. Most importantly, the biological product can be rendered substantially free of viruses that cause hepatitis and acquired immune deficiency syndrome (AIDS). A product pure of tetrameric hemoglobin and various other contaminants would have the widest clinical utility, ease of use and safety.

Insofar as the physiological properties are concerned, the biological product of this invention does not cause vasoconstriction, renal toxicity, hemoglobinurea and other problems implicated with intravenous administration of known hemoglobin solutions containing undesirable amounts of tetrameric hemoglobin. Upon intravenous administration of the product described herein, the results have demonstrated no appreciable decrease in urine production, no appreciable decrease in glomerular filtration rate, no appreciable extravasation into the peritoneal cavity and no appreciable change in the color of urine produced.

Therefore, the acellular red blood cell substitute of this invention finds usefulness in the treatment of trauma, myocardial infarction, stroke, acute anemia and oxygen deficiency disorders such as hypoxemia, hypoxia or end stage hypoxia due to impairment or failure of the lung to fully oxygenate blood. The product also finds usefulness in the treatment of any disease or medical condition requiring a resuscitative fluid (e.g., trauma, specifically hemorrhagic shock), intravascular volume expander or exchange transfusion. In addition to medical treatment, the product can be useful in preserving organs for transplants.

The present invention further encompasses methods for using this biological product for medical treatment by administering intravenously to a mammal needing such treatment a pharmaceutically effective amount of the essentially tetramer-free, substantially stroma-free, cross-linked, polymerized, pyridoxylated hemoglobin in conjunction with a nontoxic, pharmaceutically acceptable carrier. An exchange transfusion typically entails replacing the patient's blood with the acellular red blood cell substitute of this invention using conventional techniques in treatment of certain conditions or disorders such as, for example, blood poisoning, autoimmune diseases, etc. The pharmaceutically effective amount varies in relation to the therapy desired for the particular disease or medical condition being treated and typical dosage parameters, such as, for example, the body weight of the patient. Generally, the pharmaceutically effective amount is, of course, the dosage range deemed by physicians and other medical staff to be clinically useful in practice. It would be apparent to one skilled in the medical field how to select a dosage amount in any given situation. The pharmaceutically acceptable carrier is preferably nontoxic, inert and compatible with hemoglobin. Examples of such carriers include, but are not limited to, water, balanced saline solution, physiologic saline solution (e.g., Lactated Ringer's solution, Hartman's solution, etc.), dextrose solution and the like.

The preferred starting material in the process of the present invention is outdated human blood. Preferably, the blood is not used in this process if it has been in storage for more than eight weeks past the expiration date stamped on the bag. All processes described herein are applicable to other mammalian blood with possible minor modifications within the skill of the art.

The entire process may be carried out at about 2° C. to about 8° C., preferably about 5° C. The outdated blood is washed with about two to about five volumes of an isotonic salt solution such as 0.9% sodium chloride. The wash solution optionally may contain antibiotics, for example, penicillin, streptomycin, gentamycin, polymyxin B sulfate and the like. The addition of antibiotics is not essential to the process but may minimize bacterial contamination if the process is being carried out in a nonpharmaceutical environment.

The red blood cells are washed, packed, pooled and lysed with either an alkali metal phosphate buffer (e.g., sodium phosphate) or pyrogen free water. The next step is to separate the red blood cell stroma from the solution. The removal of the red cell stroma may be accomplished by microporous filtration. A preferred method is the use of cross-flow filtration with hollow fiber cartridges. Examples of cross-flow filtration systems are the Pellicon System (Millipore Corp., Bedford, Mass.); the HP-Lab 15 ultrafiltration System (Romicon Corp., Woburn, Mass.); the KF200-100 KROSFLOW (Microgon, Lagona Hills, Calif.) or the DC-30 System (Amicon, Danvers, Mass.). Systems are available for smaller or larger batch sizes than that being described in the example below.

In the next step, the stroma-free hemoglobin solution is pyridoxylated using pyridoxal, 5' phosphate on about a 2:1 to 4:1 molar ratio to hemoglobin. Pyridoxylation desirably takes place in the presence of an acid buffer such as tris-hydrochloride buffer in approximately 0.1M final concentration and about 1 gm/L of glutathione. The solution is completely deoxygenated employing a gas exchanger with helium, nitrogen or other inert gas, desirably with nitrogen gas tanks or liquid nitrogen tanks. Any tubing being used to pump the solution should preferably be impermeable or minimally permeable to oxygen, such as Tygon B-44 tubing (Cole-Palmer Co., Chicago, Ill.). A reducing agent such as sodium cyanoborohydride or preferably sodium borohydride is added to the deoxygenated solution. Excess reagents may be removed by dialysis against pyrogen free water using a kidney dialysis filter such as C-DAK 1.3 (Cordis Dow Corp., Miami, Fla.) or TH-15 (Terumo Corp., Tokyo, Japan). Alternatively, ultrafiltration cartridges with a molecular weight cut-off of no greater than 30,000 daltons can be used (cartridges are commercially available from Amicon Corp., Romicon, Millipore).

Subsequently, the stroma-free, pyridoxylated hemoglobin solution is polymerized using 25% glutaraldehyde (E. M. Grade, Polysciences, Warington, Pa.). The stroma-free, pyridoxylated hemoglobin solution is exposed to the glutaraldehyde across a kidney dialysis filter or other suitable membrane filter. The duration of polymerization and the amount of glutaraldehyde added is dependent on volume of the hemoglobin solution, the desired yield of polymers and the desired molecular weight distribution. In general, the longer the polymerization time, the higher the molecular weight distribution of polymers, the greater their yield and lower the COP of the final solution. Typically, approximately a 70% yield of polymers is obtained in 3.5–4 hours. This is the preferred end point of the polymerization. An 80–90% yield can be obtained in 7 hours but will result in a significantly higher molecular weight distribution of the polymers (FIG. 3C).

The polymerizing process when carried out according to the present invention results in a high yield of polymers. To produce a product with reliable clinical utility, it is very important to control the speed of reaction and surface of interaction during polymerization so as to produce a product of a narrow molecular weight range, the average of which is about 120,000 daltons. The polymerization reaction may be monitored by the decrease in colloid osmotic pressure using an oncometer, such as IL 186 (Instrumentation Laboratories, Danvers, Mass.) or Wescor Colloid Osmometer (Wescor, Logan, Utah), by High Pressure Liquid Chromatography (HPLC) or by any appropriate technique known in the art. Trace amounts of high molecular weight molecules may be present as determined by sodium dodecyl sulfate polyacrylamide gel electrophoresis (SDS-PAGE).

At the semi-permeable membrane interface in the pyridoxylating and polymerizing steps of the process of this invention, the biochemical carrier (i.e., water, salts, sugars, other small molecules or ions) is very free to move back and forth across the membrane in response to hydrostatic, hydrodynamic, osmotic or oncotic forces. The molecules or ions of the active agent (i.e., polymerizing agents, reducing agents, pyridoxylating agents, etc.) are somewhat less free to move across the membrane owning to their greater size and weight. The hemoglobin molecules cannot cross the intact membrane at all. This set-up results in a controlled exposure of hemoglobin molecules or other starting materials to the active agent. The variables that can be altered are now rate of the hemoglobin solution, concentration of hemoglobin in solution, concentration of the active agent and flow rate of the active agent. In addition to the above variables, variables such as time, temperature and surface area can be altered to modify this set-up for a wide range of reactants, reactions and efficiencies. The entire reaction can take place in a physiologically acceptable medium. Further, the hemoglobin solution can move through the reaction without experiencing any significant changes in dilution or ionic environment.

Schematically, FIG. 1 shows the batch method of pyridoxylation. A solution of stroma-free hemoglobin and reagents containing pyridoxal, 5', phosphate 6 is added to the mixing vessel or container 5. The pH is adjusted and monitored by a pH electrode 7. The container 5 has a vent or bleed valve 11. A means for stirring such as a toroidal mixer comprising an electric motor 9, universal joint couplers 9a for coupling the motor shaft to the mixing shafts and stirrer 10 provides continual mixing. The solution 6 is pumped out of the container 5 by means for pumping 4 through a membrane gas exchanger 1 and is then returned to container 5. A nitrogen source 8 supplies a constant flow of nitrogen through the membrane gas exchanger 1 to deoxygenate the solution 6. The membrane gas exchanger 1 contains vent 3 for release of gases. A solution containing a reducing agent is added through syringe port 2. Circulation of the solution of deoxygenated hemoglobin continues around this set-up through constant pumping action provided by pumping means 4 until the desired yield of pyridoxylated hemoglobin is obtained.

FIG. 2 illustrates a schematic diagram of pyridoxylation and polymerization respectively using the membrane technique in accordance with this invention. For pyridoxylation, a solution of stroma-free hemoglobin and reagents containing pyridoxal, 5', phosphate 19 is added to the mixing vessel or second reservoir 18. The second reservoir 18 has a vent or bleed valve 17. A means for stirring such as a toroidal mixer comprising an electric motor 16, universal joint couplers 16a and stirrer 20 provides continual mixing.

Initially, the solution 19 is continuously pumped through two deoxygenating pathways while ports 31 and 32 are clamped shut. Simultaneously, the solution 19 is pumped out of the second reservoir 18 by means for pumping 15 through a membrane gas exchanger 13 and by means for pumping 21 through a membrane gas exchanger 23 and a renal dialysis membrane filter 27 and then is returned to the second reservoir 18. Nitrogen sources 12 and 24 supply a constant flow of nitrogen through membrane gas exchangers 13 and 23, respectively, to deoxygenate solution 19. The membrane gas exchangers 13 and 23 contain vents 14 and 22 for release of gases. The pH is monitored by pH electrode 25 through an electrical lead 26 attached to a pH meter. After deoxygenation, ports 31 and 32 are opened. A solution containing a reducing agent 30 is pumped by means for pumping 28 from container or first reservoir 29 through the renal dialysis membrane filter 27 and is returned to the first reservoir 29.

After pyridoxylation is completed, the solution containing the reducing agent 30 is replaced by pyrogen-free water. The pyrogen-free water is then pumped by means for pumping 28 through the renal dialysis membrane filter 27 to dialyze excess reagents and is returned to the first reservoir 29. Ports 31 and 32 are closed by clamps and solution 19 is circulated continuously while being deoxygenated.

For polymerization, ports 31 and 32 are opened. The solution of stroma-free, pyridoxylated hemoglobin 19 is constantly circulated through the set-up. The pyrogen-free water in the first reservoir 29 is replaced by a polymerizing solution containing a polymerizing agent 30. The polymerizing solution is then pumped by means for pumping 28 through the renal dialysis membrane filter 27 and is returned to the first reservoir 29. As depleted, the polymerizing agent is added stepwise to the first reservoir.

Basically, the solution containing a reducing agent for pyridoxylation or the polymerizing solution containing a polymerizing agent is pumped from a first reservoir 29 to one side of a semipermeable membrane in the renal dialysis membrane filter 27 while the deoxygenated hemoglobin solution or pyridoxylated, deoxygenated hemoglobin solution, respectively, is pumped from a second reservoir 18 to the opposite side of the membrane. A portion of the solution containing a reducing agent or polymerizing agent diffuses across the membrane to pyridoxylate or polymerize the hemoglobin on the other side of the membrane. The portion of the solution containing a reducing agent or polymerizing agent which does not diffuse is returned to the first reservoir 29. Likewise, the deoxygenated hemoglobin solution containing either the pyridoxylated or polymerized hemoglobin is returned to the second reservoir 18. This operation works continuously until the desired yield of product has been obtained.

At the termination of the polymerization, the unpolymerized tetrameric hemoglobin concentration in the solution can be decreased significantly by any appropriate filtering and purifying techniques known in the art. Removal of essentially all of the remaining unmodified tetramer may be accomplished by pumping the polymerized solution through hollow fiber ultrafiltration cartridges and then purifying by gel chromatography or, alternatively, by gel chromatography alone.

The remaining traces of unmodified tetrameric hemoglobin can be complexed in accordance with this invention by adding haptoglobin alone, treating with haptoglobin after using hollow fiber ultrafiltration cartridges and/or gel chromatography or removing by affinity chromatography using gel bound haptoglobin. Haptoglobin will bind irreversibly with tetrameric hemoglobin even in the presence of polymerized hemoglobin. Haptoglobin will bind hemoglobin on a 1:1 molar ratio. One would require 1.3–1.5 gm of haptoglobin to bind 1 gm of hemoglobin if the complexing is being conducted in a free solution. Alternatively, haptoglobin can be bound to an activated agarose gel.

The pH of the final solution is adjusted to approximately 9 and balanced with electrolyte concentrations representing that of normal plasma. For clinical use, electrolytes which may be added include, but are not limited to, sodium, potassium, chloride, calcium, magnesium and the like. Conventional anti-oxidants such as glutathione, ascorbate or glucose may also be optionally added. The final solution may be sterilized using any well-known technique appropriate for application to biological products.

The critical properties of the solution of this invention in approximate amounts or ranges are shown along with that of whole blood for purposes of comparison:

|  | Polymerized Hb | Whole Blood |
| --- | --- | --- |
| Hb | 7–18 gm/dl | 12–15 gm/dl |
| $O_2$ Carrying Capacity | 9.7–25.0 vol % | 16.6–20.9 vol % |
| Binding Coefficient (at 37° C.) | 1.30 cc/gm Hb | 1.32 cc/gm Hb |
| $P_{50}$ (at $pCO_2$ 40 torr, pH 7.4, 37° C.) | 14–22 torr | 26 torr |
| Methemoglobin | less than 15% | less than 2% |
| Colloid Osmotic Pressure | 7–30 torr | 20–25 torr |
| Osmolarity | 290–310 mOsM | 290–310 mOsM |
| Total Phospholipid Content | less than 0.004 mg/ml |  |
| Viscosity (at 25° C.) | 3.2 cp (8 gm/dl) | 3.5 (Hct = 45%) |

The following examples demonstrate certain aspects of the present invention. However, it is to be understood that these examples are for illustrative purposes only and do not purport to be wholly definitive as to conditions and scope of this invention. All temperatures are expressed in degrees Celsius unless otherwise specified. It also should be appreciated that when typical reaction conditions (e.g., temperature, reaction times) have been given, the conditions which are both above and below these specified ranges can also be used, though generally less conveniently.

A further understanding of the invention may be obtained from the following nonlimiting examples. These examples were conducted at about 5° C. and at atmospheric pressure:

EXAMPLE 1

Preparation of Stroma-Free Tetrameric Hemoglobin Solution

Outdated human blood was washed twice with 0.9% sodium chloride solution containing the following antibiotics per liter of solution:

| Penicillin | 50,000 U |
| --- | --- |
| Streptomycin | 50 mg |
| Gentamycin | 40 mg |
| Polymixin B Sulfate | 2.5 mg |

The red blood cells (RBC) were washed twice with equal volumes of the above solution and centrifuged at 2,500 g for 15 minutes. Better than 95% of the buffy coat layer was removed with a plasma extractor (Fenwal Laboratories, Morton Grove, Ill.). The washed and packed RBCs were then pooled and lysed with 3 to 4 volumes of pyrogen free water. One hundred units of washed RBCs resulted in a 15–20 L volume at a hematocrit of 20–24%.

Fifteen to twenty liters of washed RBCs were poured into 40–80 liters of cold pyrogen free water. The lysate thus made, was then pumped through 2 to 4 $0.1\mu$ hollow fiber cartridges. An air driven pump was used (LP30, Amicon Corp., Danvers, Mass.). The $0.1\mu$ cut-off cartridges were commercially available from Romicon Inc., subsidiary of Rohm and Haas Co., Woburn, Mass. 01801. The hemoglobin, essentially free of RBC stroma, along with the other enzymic contents of the RBC came through the filter as an ultrafiltrate. Aliquots of the filtrate were centrifuged several times during this process. Absence of a pellet reflected good membrane integrity. A 97% recovery of essentially stroma-free hemoglobin was obtained.

During this first separation step, the lysate volume was reduced down to 12–15 liters, and maintained at that volume by addition of pyrogen free water until the necessary recovery of hemoglobin had been effected. Simultaneously with the step, the ultrafiltrate containing the hemoglobin was concentrated, with the aid of 3 to 4 30 k cut-off hollow fiber cartridge filters (H10 P30, Amicon Corp., Danvers, Mass.) and an LP 30 air pump. The ultrafiltrate was concentrated to a final hemoglobin concentration of about 20–22 gm/dl.

EXAMPLE 2

Preparation of Stroma-Free Tetrameric Hemoglobin Solution—an Alternative Method

Individual units of outdated blood were filled with 0.9% sodium chloride solution. The red cells and buffy coat were allowed to settle overnight. The supernatant and buffy coat were then extracted.

The packed cells were then poured into 3–5 volumes of 0.9% sodium chloride solution. The cells were washed and concentrated by use of a $0.2\mu$ hollow fiber cross-flow filter (K205—KROSFLOW, Microgon Corp., Laguna Beach, Calif.) and an air driven pump (LP30, Amicon Corp., Danvers, Mass.). The packed cells were then lysed by the addition of 3–5 volumes of pyrogen free water. The cross-flow filtration was then resumed, with the tetrameric hemoglobin along with the enzymic contents of the red cells being collected in the ultrafiltrate, while the stroma was retained by the filter.

Aliquots of the filtrate were centrifuged several times during this process. Absence of a pellet reflected good membrane integrity. A 97% recovery of essentially stroma-free hemoglobin was obtained. Simultaneously with the step, the ultrafiltrate containing the hemoglobin was concentrated, with the aid of 3 to 4 30 k cut-off hollow fiber cartridge filters (H10 P30, Amicon Corp., Danvers, Mass.) and an LP 30 air pump. The ultrafiltrate was concentrated to a final hemoglobin concentration of about 20–22 gm/dl.

EXAMPLE 3

Pyridoxylation of the Stroma-Free Hemoglobin—Mixed Batch Geometry

A stroma-free hemoglobin solution was prepared according to the process of Example 1 or 2. The following reagents were mixed together:

1. Pyridoxal, 5', phosphate—on a 4:1 molar ratio to hemoglobin;
2. Tris-HCl buffer—0.1M final concentration in the hemoglobin solution;
3. Glutathione—1 gm/L of solution;
4. Ascorbic Acid—0.2 gm/L;
5. Glucose 0.5 gm/L; and
6. Antibiotics—the same antibiotics as described in Example 1.

The above reagents were dissolved in minimal volume of pyrogen free water and the pH adjusted to 7.25–7.45. The above mixture was added to the hemoglobin solution. The pH of the hemoglobin solution was adjusted to 7.35–7.45 at 5° C. with 0.1 N NaOH. Finally, the hemoglobin concentration was adjusted to 17.5–18.5 gm/dl.

The solution (18–20 L) was then transferred to a gas tight stainless steel reservoir. Deoxygenation of the solution was accomplished by use of a membrane gas exchanger (William Harvey, Bently Laboratories, Shiley Sales Corp., Irvine, Calif.). Nitrogen gas was bubbled through the exchanger at a flow rate of about 170 L/min. The hemoglobin solution was pumped through the gas exchanger at a flow rate of 4–6 L/min. Adequate removal of oxygen was defined as an $O_2$ saturation, of less than 5% and an oxygen content of less than 1 vol % (by the IL 282, Co-oximeter, Instrumentation Laboratories, Lexington, Mass.). This was accomplished in 4–8 hours (see FIG. 1).

To the deoxygenated hemoglobin solution, 0.02 M sodium borohydride (final concentration) per liter of solution was added. The sodium borohydride was dissolved in no less than 300–500 ml of 0.001 N NaOH. It was pumped into the hemoglobin solution, through a syringe port of the gas exchanger, at a rate of about 100 ml/hr. A bleed valve in the stainless steel reservoir was kept open to avoid pressure build-up. Following the addition of $NaBH_4$, the solution was kept deoxygenated. A maximal yield of about 70–80% of pyridoxylated hemoglobin was obtained in 6–10 hours. The yield was determined by measuring the shift in the oxygen-hemoglobin dissociation curve ($P_{50}$).

The excess reagents were removed by dialysis against pyrogen free water using a kidney dialysis filter (C-DAK 1.3, Cordis Dow Corp., Miami, Fla. or TH-15, Terumo, Tokyo, Japan). The solution was kept deoxygenated during dialysis by keeping a membrane oxygenator in line. The $N_2$ flow rate through the oxygenator was about 100 L/min.

EXAMPLE 4

Pyridoxylation of the Stroma-Free Hemoglobin—Membrane Facilitated Geometry

A stroma-free hemoglobin solution was prepared according to the process of Example 1 or 2. The following reagents were mixed together:

1. Pyridoxal, 5', phosphate—on a 2:1 molar ratio to hemoglobin;
2. Tris-HCl buffer—0.1M final concentration in the hemoglobin solution;
3. Glutathione—1 gm/L of solution;
4. Ascorbic Acid—0.2 gm/L;
5. Glucose 0.5 gm/L; and
6. Antibiotics—the same antibiotics as described in Example 1.

The above reagents were dissolved in minimal volume of pyrogen free water and the pH adjusted to 7.35–7.45. The above mixture was added to the hemoglobin solution. The pH of the hemoglobin solution was adjusted to 7.35–7.45 at 5° C. with 0.1 N NaOH. The hemoglobin concentration was adjusted to 17.5–18.5 gm/dl.

The solution (18–20 L) was then transferred to a gas tight stainless steel reservoir. Deoxygenation of the solution was accomplished by use of one or more membrane gas exchangers (William Harvey, Bently Laboratories, Shiley Sales Corp., Irvine, Calif.). Nitrogen gas was bubbled through the exchanger at a flow rate of about 170 L/min. The hemoglobin solution was pumped through the gas exchanger at a flow rate of 4–6 L/min. Adequate removal of oxygen was defined as an $O_2$ saturation, of less than 5% and an oxygen content of less than 1 vol % (by the IL 282, Co-oximeter, Instrumentation Laboratories, Lexington, Mass.). This was accomplished in 4–8 hours.

In this process, the membrane oxygenator or gas exchanger 23 was in series with a kidney dialysis filter 27 (Terumo, TH-15) (see FIG. 2). The external parts of the dialysis filter were clamped to prevent loss of water during deoxygenation.

When the end point of the deoxygenation was reached, 3 liters of a 5 gm % sodium borohydride solution was pumped on the outside of the dialysis filter. In this fashion, the pyridoxylation was rapidly accomplished. A 75–80% yield of pyridoxylated hemoglobin was obtained in half an hour, and a maximal yield of 85–90% was obtained in 2–3 hours. The yield was determined by measuring the shift in the oxygen-hemoglobin dissociation curve ($P_{50}$).

The excess reagents were removed by dialysis against pyrogen free water using the in-line kidney dialysis filter (C-DAK 1.3, Cordis Dow Corp., Miami, Fla. or TH-15, Terumo, Tokyo, Japan). The solution was kept deoxygenated during dialysis. The $N_2$ rate through the oxygenator was about 100 L/min.

EXAMPLE 5

Polymerization of Stroma-Free Pyridoxylated Hemoglobin

A stroma-free, pyridoxylated hemoglobin solution was prepared according to the process of Example 3 or 4. To the dialyzed solution was added:

1. 0.1 M sodium phosphate buffer (final concentration);
2. Antibiotics as listed above in Example 1; and
3. Glutathione—1 gm/L.

The above chemicals were dissolved in 500 ml of pyrogen free water and added to the hemoglobin solution. The pH of the solution, at 5° C. and using 0.5 N NaOH, was adjusted to 8.0. The hemoglobin concentration was adjusted to between 14–15 gm/dl by the addition of 0.1 M phosphate buffer. The solution was maintained deoxygenated by keeping the membrane oxygenator in line. An $N_2$ flow rate of about 170 L/min was maintained.

The hemoglobin solution was pumped from the mixing vessel or second reservoir 18 through the membrane oxygenator or gas exchanger 23 into a kidney dialysis filter 27 (see FIG. 2) at an approximate flow rate of 5–7 L/min. Sampling was done through the syringe port on the oxygenator. Polymerization was not initiated if the percent oxyhemoglobin was greater than 10% as determined by co-oximetry. The solution was polymerized across the kidney dialysis membrane. The polymerizing solution was made up in a 10 L volume and contained:

1. 0.1 M sodium phosphate buffer (same final concentration as in the hemoglobin solution);
2. Antibiotics—same concentration as in hemoglobin solution;
3. Glutathione—1 gm/L; and
4. 175–225 ml of 25% Glutaraldehyde solution (about 14.8–18.1 moles glutaraldehyde per mole hemoglobin).

The osmolarity of the polymerizing solution was about the same as that of the hemoglobin solution.

The flow of the deoxygenated hemoglobin solution was first established through the dialysis filter while pyrogen free water was circulating on the outside. Once the required flow rate was set, the polymerizing solution was then circulated on the outside. The solution was pumped (Cole-Palmer pumps, 7018 pump heads) at an approximate flow rate of 0.4–0.6 L/min. The hemoglobin solution in the reservoir was thoroughly mixed throughout the process.

The polymerizing agent (25% Glutaraldehyde) was subsequently added to the polymerizing solution according to the following schedules:

| Time 1 hour  | –75 ml |
|--------------|--------|
| Time 2 hours | –50 ml |
| Time 3 hours | –50 ml |
| Time 4 hours | –50 ml |
| Time 5 hours | –50 ml |
| Time 6 hours | –25 ml |
| Time 7 hours | –10 ml |

The polymerization was monitored by the drop in colloid osmotic pressure (COP). The reaction was stopped when the COP approached about 40 torr. This was accomplished by draining the outside of the dialysis filter of the polymerizing solution, and pumping in pyrogen free water. Dialysis against pyrogen free water was carried out for approximately 2 hours. Approximately 80–90% yield of polymers was obtained.

EXAMPLE 6

Ultrapurification of Stroma-Free, Polymerized, Pyridoxylated Hemoglobin

A stroma-free, polymerized, pyridoxylated hemoglobin solution was prepared according to the procedure of Example 5. The removal of the unmodified tetramer was accomplished in three steps:

Step 1: Ultrafiltration

The polymerized solution was pumped through 3 to 4 hollow fiber ultrafiltration cartridges with a molecular weight cut-off of 100,000 daltons (Amicon). This step was stopped when the hemoglobin concentration in the ultrafiltrate was well below 0.1% and stayed at that level for at least two hours. The polymerized hemoglobin solution at this stage was approximately 90% pure.

Step 2: Gel Filtration

The second purification step resulting in an approximately 95–98% pure polymeric solution was accomplished by gel chromatography as follows:

Two 60 cm×25 cm chromatography bioprocess columns (Pharmacia Fine Chemicals, Piscataway, N.J.) were filled with approximately 55 L of ACA-54 Ultrogel (LKB Instruments, Gaithersburg, Md.). This gel had a molecular weight exclusion limit of 90,000 daltons. The columns were connected in series with minimal dead space between them, resulting in an effective gel length of approximately 105 cm.

Figure 4:
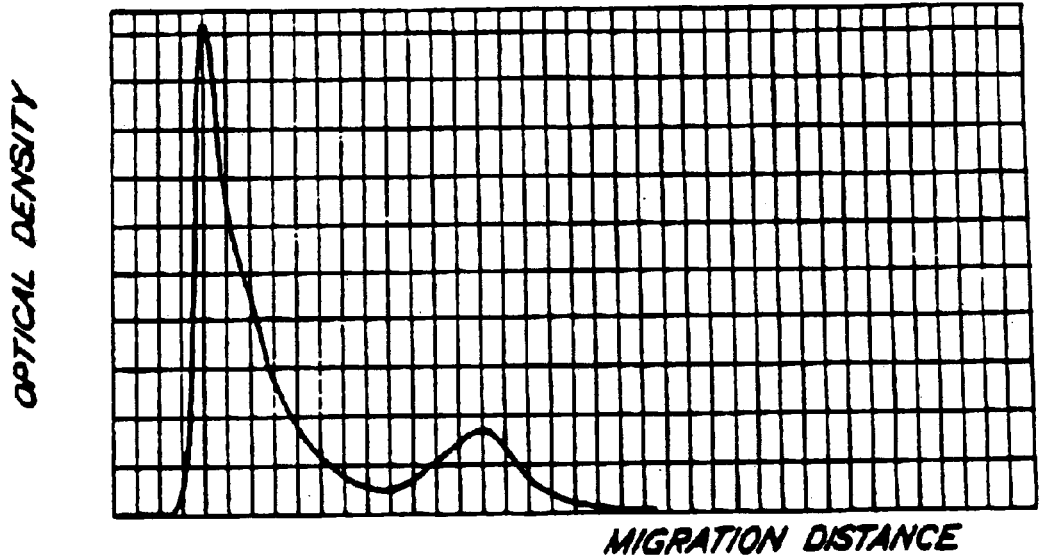
FIG. 4 shows an elution pattern of cross-linked, polymerized, pyridoxylated hemoglobin obtained from a gel filtration column.
Figure 5:
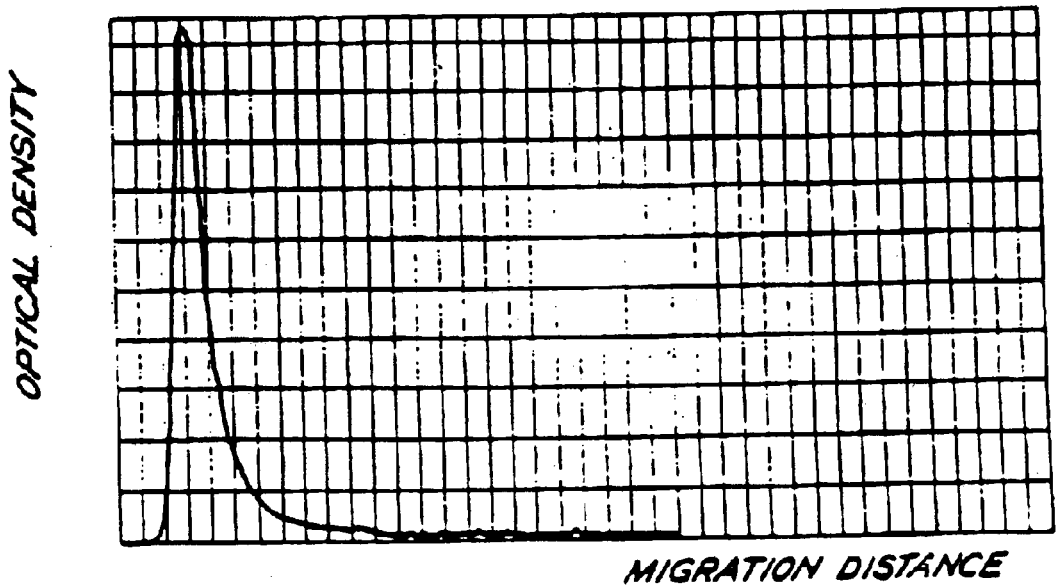
FIG. 5 shows an elution pattern of essentially tetramer-free, cross-linked, polymerized, pyridoxylated hemoglobin obtained from a gel filtration column.

One half to one liter of the polymerized hemoglobin solution from step 1 with a hemoglobin concentration of 6–10 gm/dl was loaded onto the column at a flow rate of approximately 3 L/hr. Subsequent to the loading, the buffer (0.1 M sodium phosphate pH 7.40 at 5° C.) was used to elute the hemoglobin at a flow rate of 3.0 L/hr (FIG. 4). The first 2.0 L of the polymerized hemoglobin solution that was eluted from the column was retained. The remaining solution was discarded. The 2 L fraction from the column was concentrated using the Amicon CH-2 ultrafiltration system with 1 to 3 H1P100 cartridges (FIG. 5). The ultrapurified solution was concentrated. Step 2 was repeated as necessary to reduce the tetramer contamination of the polymerized solution.

Step 3: Affinity Chromatography

Haptoglobin (Hp) was bound to an activated agarose gel as follows:

Haptoglobin (greater than 80% pure) was added to CnBr activated Sepharose 4B (Pharmacia Fine Chemicals, Piscataway, N.J.), in a ratio of 3 mg Hp/ml sedimented gel. Four volumes of coupling buffer (0.1 M sodium bicarbonate, 0.3 M NaCl, pH 7.9) was added per volume of sepharose. The mixture was stirred gently overnight at 4° C. The yield of this reaction was 2 mg Hp/ml sedimented gel. An excess of the Hp affinity gel (with respect to the free tetrameric hemoglobin) was added to the polymerized, pyridoxylated hemoglobin solution and stirred gently at 4° C. for 1–4 hours. The solution was then centrifuged gently (4000 g for 2 minutes) and the supernatant recovered. Additional washes and centrifugations were carried out to maximize recovery of the polymerized hemoglobin. The polymerized, pyridoxylated hemoglobin thus obtained was greater than 99.5% free of unmodified tetrameric hemoglobin.

Alternative Step 3: Complexing with Haptoglobin

The final traces of unmodified tetrameric hemoglobin were removed from the polymerized, pyridoxylated hemoglobin solution by complexing it with haptoglobin (Hp). Haptoglobin was added on a 1:1 molar ratio to free tetrameric hemoglobin. The solution was mixed at room temperature for approximately 2 hours.

EXAMPLE 7

Pharmaceutical Composition of Ultrapurified, Stroma-Free, Polymerized, Pyridoxylated Hemoglobin An ultrapurified stroma-free, polymerized, pyridoxylated hemoglobin solution was prepared according to the procedure of Example 6. The pH of the solution at 5° C. using 0.5 N NaOH was adjusted to about 9.02 and balanced with an electrolyte concentrate to yield the following concentrations in the final solution:

| | |
|---|---|
| Na | 140 mEq/L |
| K | 4.0 mEq/L |
| Cl | 100 mEq/L |
| $Ca^{++}$ | 5.0 mEq/L |
| Mg | 1.5 mEq/L |
| Glutathione | 1 gm/L |

An enzyme cocktail was added to the solution to stabilize it against oxidation. It contained approximately no less than the stated amounts per liter of the final solution:

1. Glucose—6—Phosphate—0.3 gm
2. Glucose—6—Phosphate Dehydrogenase—0.20 mg
3. Ferrodoxin—6 mg
4. Ferrodoxin NADP Reductase—3 mg
5. NADP—40 mg
6. Catalase—0.2 gm The final hemoglobin concentration was adjusted between 7–18 gm/dl.

EXAMPLE 8

Sterilization Technique

The purified polymerized, pyridoxylated hemoglobin prepared according to the procedure of Example 6 was sterilized using the following filtration scheme with the Pall Profile Filters (Pall Corp., Glen Cove, N.Y.):

| 010→ | 007→ | 005→ | NR7P.(0.2 µ absolute). |
|---|---|---|---|
| 1 µ | 0.7 µ | 0.5 µ | 0.2 µ |

The filter medium was polypropylene. The final 0.22µ sterilizing filter was nylon. All filters were pharmaceutical grade.

The solution thus sterilized showed no growth on blood agar plates (37° C./4 days or 25° C./10 days) or in thioglycollate broth. The solution had trace amounts (0.25 ng/ml) of endotoxin, based on Limulus Amoebacyto Lysate Test, when prepared in a nonpharmaceutical environment.

EXAMPLE 9

Biochemical Characteristics

Figure 6A:
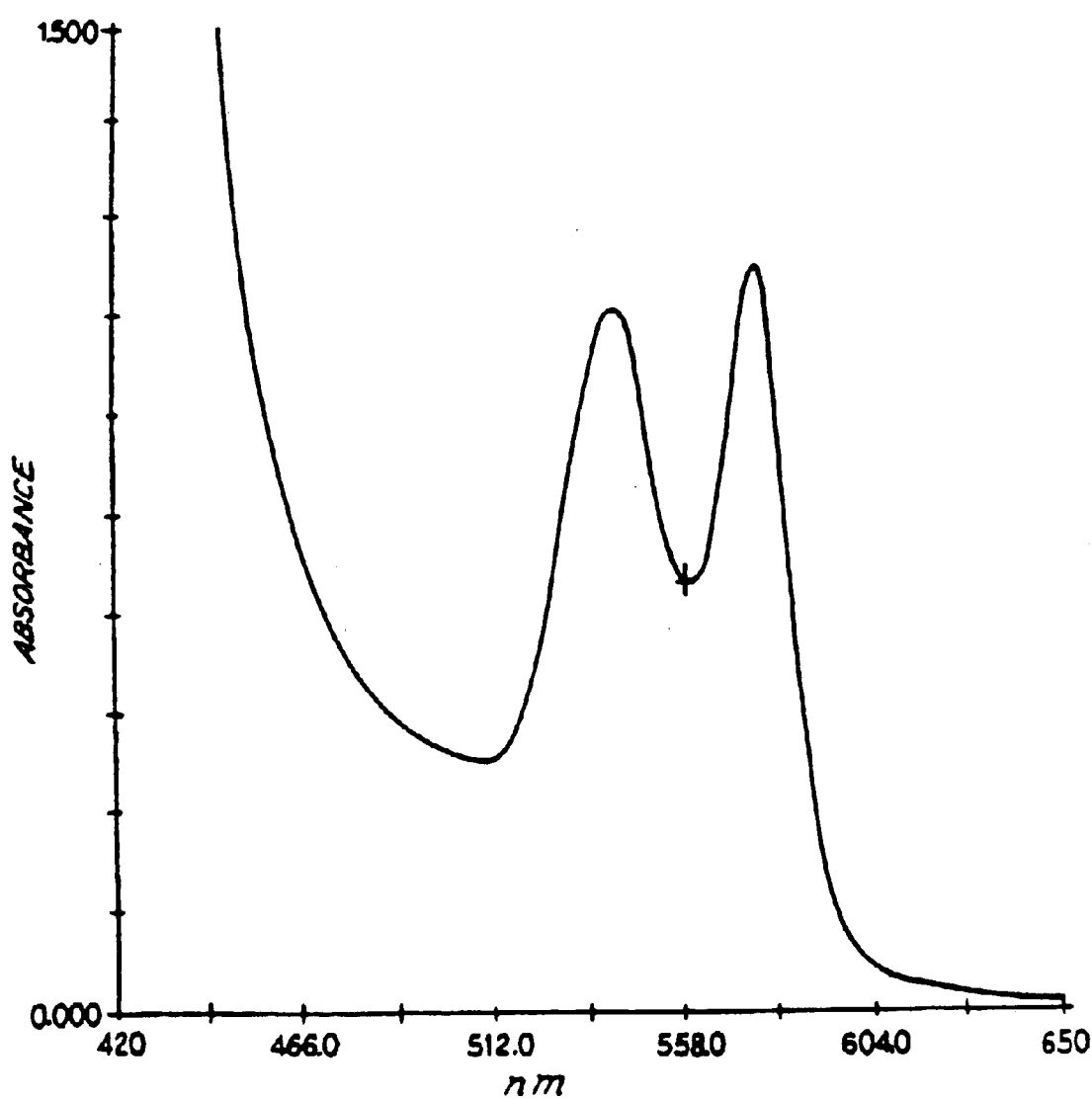
FIG. 6A is a graph showing the spectral curve for oxyhemoglobin.
Figure 6B:
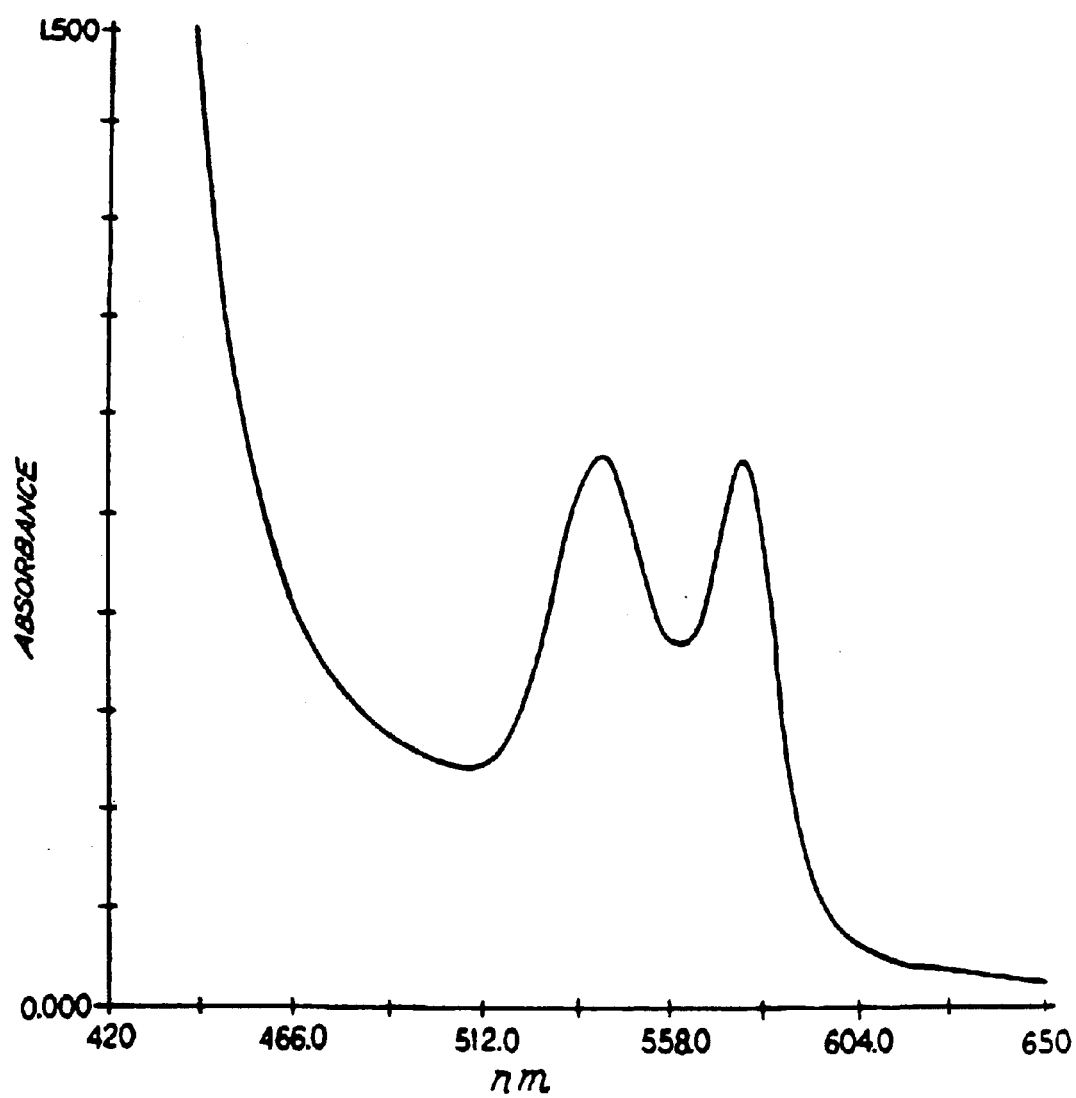
FIG. 6B is a graph showing the spectral curve obtained with oxygenated essentially tetramer-free, cross-linked, polymerized, pyridoxylated hemoglobin.
Figure 7:
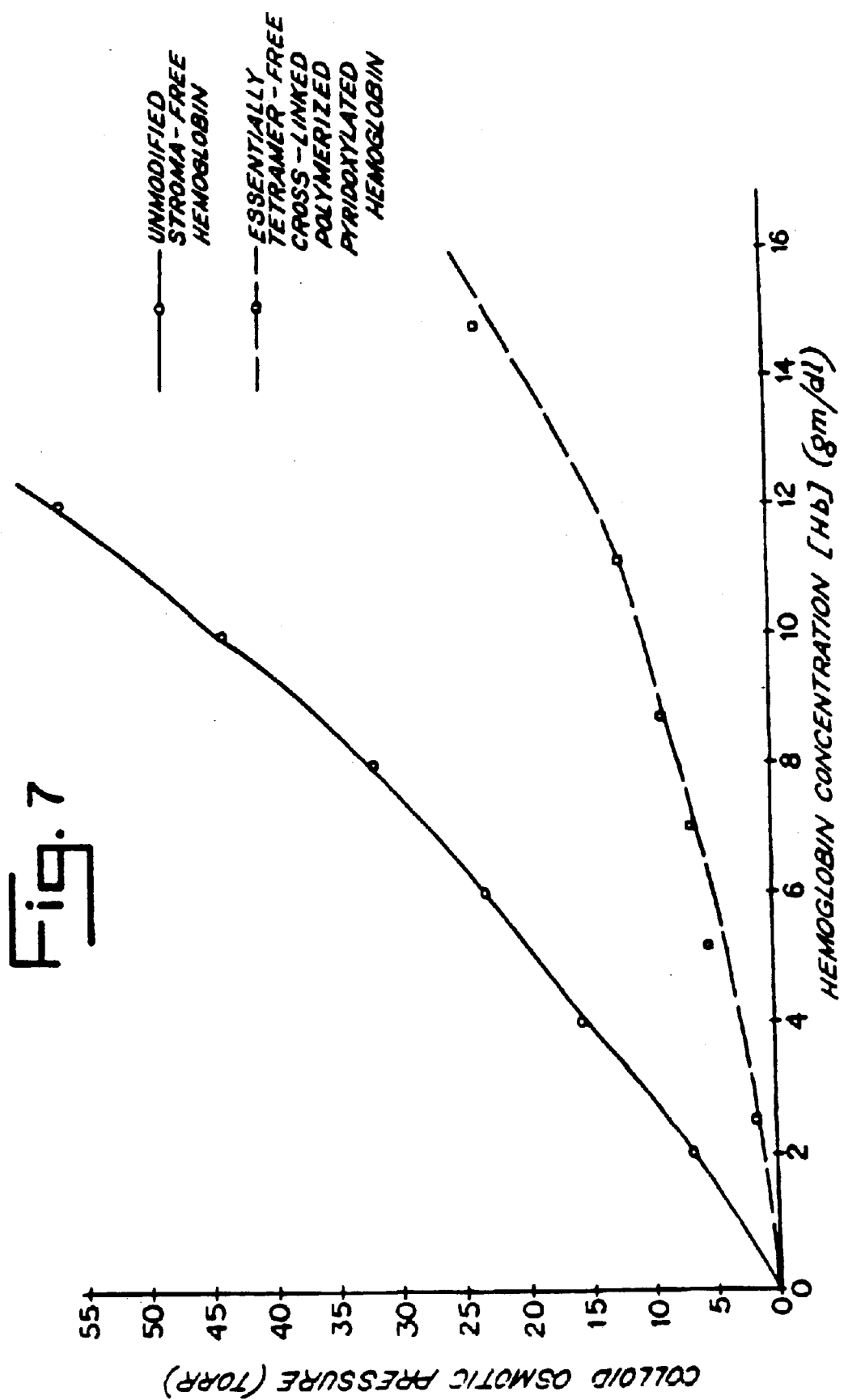
FIG. 7 is a graph describing the relationship between the hemoglobin concentration of the essentially tetramer-free, cross-linked, polymerized, pyridoxylated hemoglobin and the colloid osmotic pressure (COP)

The tetramer free polymerized, pyridoxylated hemoglobin showed a normal absorption spectrum obtained from a Beckman DU recording spectrophotometer (Beckman Instruments, Lineolnwood, Ill.) (FIG. 6B). The solution when reconstituted to a normal hemoglobin concentration (12–14 gm/dl) resulted in a solution with acceptable colloid osmotic pressure (COP) (14.5–22.5 torr) (FIG. 7). For purposes of FIG. 7, the hemoglobin concentration was determined on the IL 282 Co-oximeter (Instrumentation Laboratories, Danvers, Mass.). The COP was measured on the Wescor Colloid Osmometer Model 4400 (Boyce Scientific Inc., Hanover Park, Ill.). For purposes of comparison, the curve obtained with the unmodified stroma-free hemoglobin (SFH) is also shown. The process of polymerization did not alter the oxygen binding capacity of the hemoglobin (1.30 cc/gm). The product when reconstituted to a normal hemoglobin concentration had a normal oxygen carrying capacity.

Figure 8:
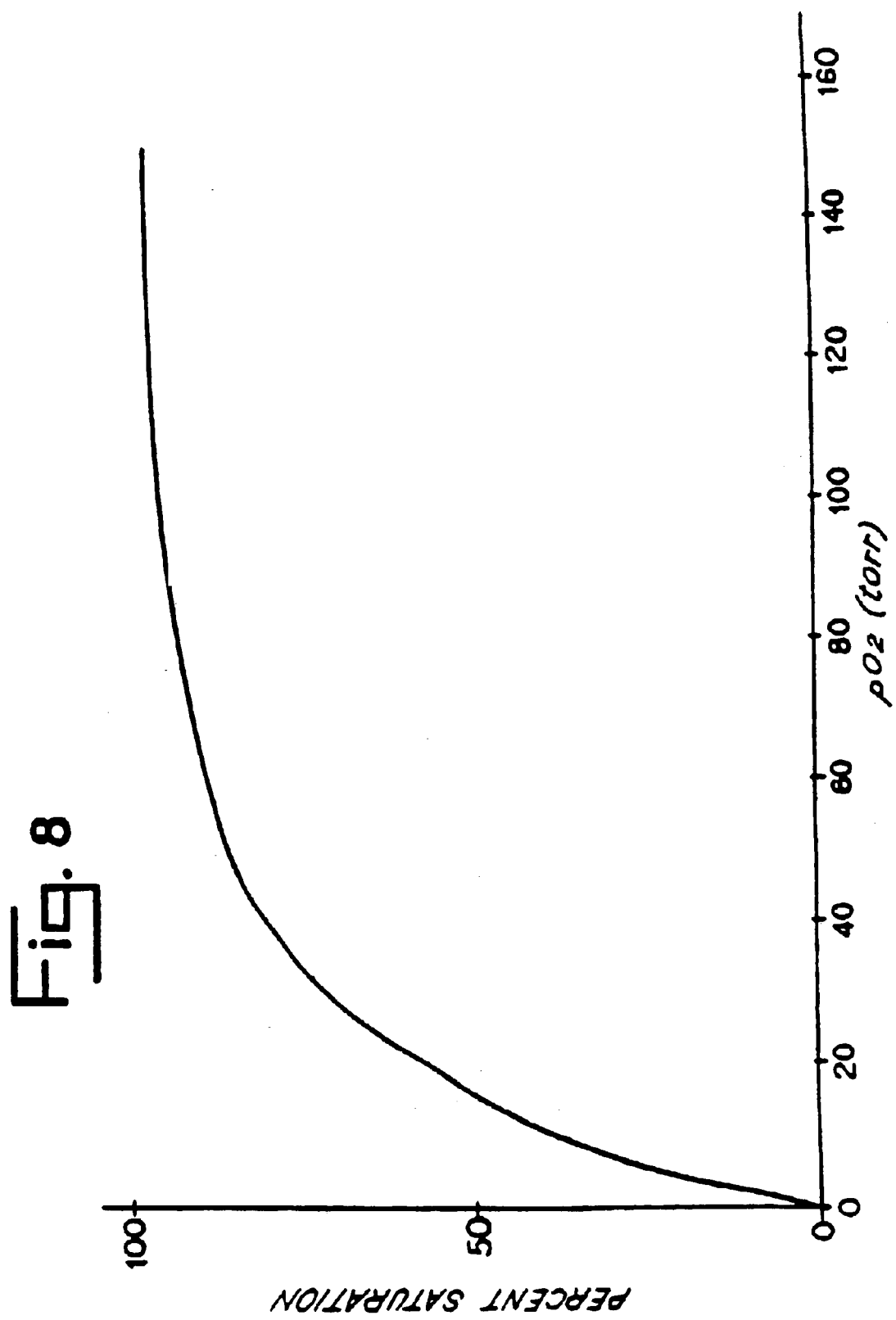
FIG. 8 is a graph describing the oxy-hemoglobin dissociation curve for an essentially tetramer-free, cross-linked, polymerized, pyridoxylated hemoglobin.

The $P_{50}$ of the product ranged from 14–22 torr when determined under physiologic conditions of pH, $pCO_2$ and temperature. A typical oxy-hemoglobin dissociation curve for the product is shown in FIG. 8. The sample was run under standard conditions of pH 7.40, temperature 37° C. and $pCO_2$ 40 torr. The continuous curve was generated by the Hem-O-Scan oxygen dissociation analyzer (Travenol Laboratories, Deerfield, Ill.).

Figure 9:
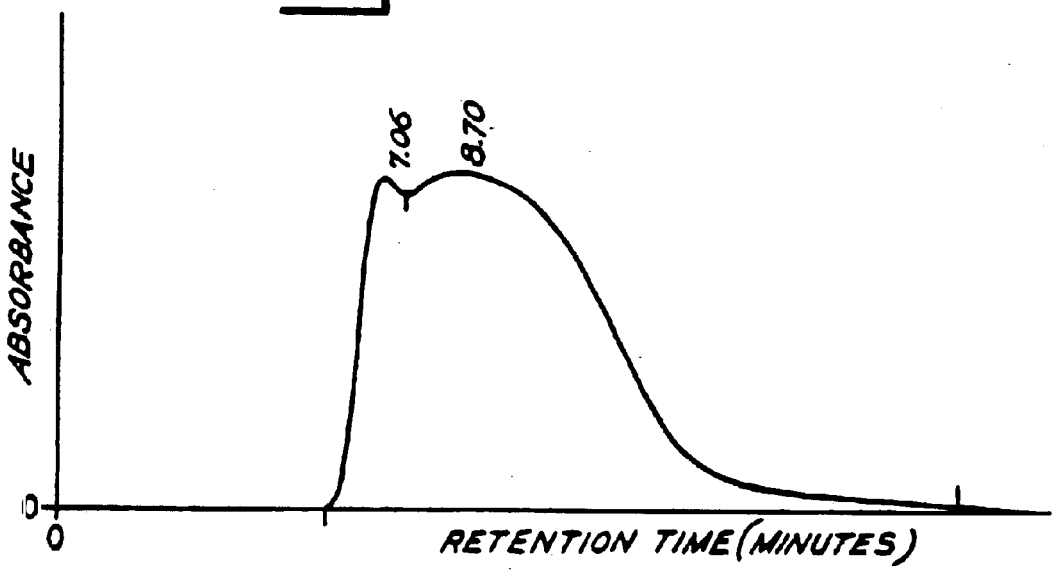
FIG. 9 is a graph describing the elution pattern of essentially tetramer-free, cross-linked, polymerized, pyridoxylated hemoglobin from a High Pressure Liquid Chromatography column.

The molecular weight distribution of the product based on HPLC appeared to range from 120,000 to 600,000 daltons (FIG. 9). The average molecular weight estimated from the data was about 120,000. FIG. 9 describes the elution pattern from an HPLC column (TSK Gel, type G 4000 S.W., Varian Instruments Group, Palo Alto, Calif.). The elution buffer used was 0.1 M sodium phosphate, pH 7.0 (at 25° C.) with 0.1 M sodium chloride (osmolarity=353 mOsm). The hemoglobin concentration of the sample is adjusted to approximately 3.0 gm/dl. Sample volume injected was 0.1 ml. Flow rate was 1 ml/min. (the HPLC pump (Model 2150), UV monitor (Model 2238 Uvicord SII) and recording integrator (Model 2220) were manufactured by LKB Instruments, Gaithersburg, Md.).

Figure 3B:
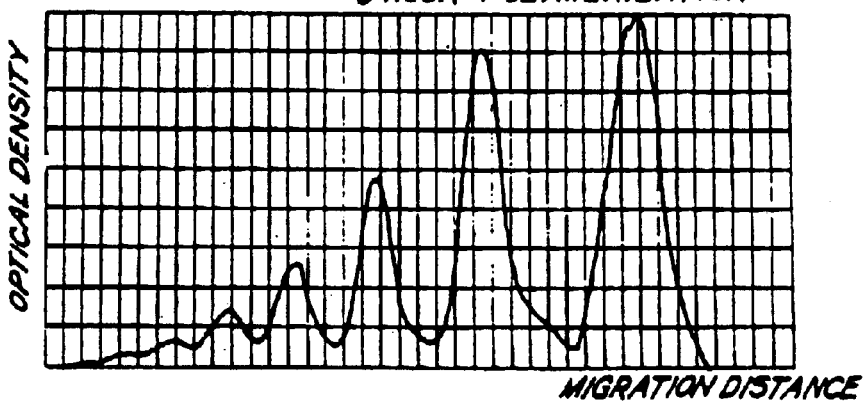
Figure 3C:
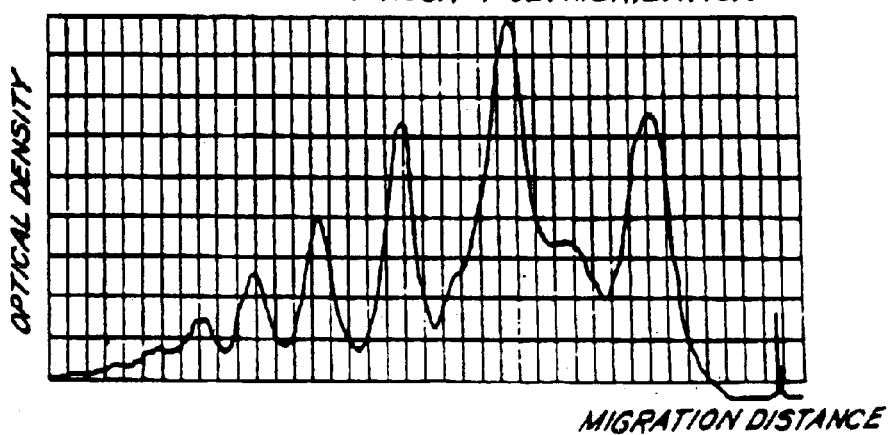

The product characterized by SDS-PAGE showed 4 polymeric bands (FIG. 3A). They represented about 58% at a molecular weight of 120,000, 26% with a molecular weight of 192,000, 11% with a molecular weight of 256,000 and 4% with a molecular weight of 320,000. Trace amounts of higher molecular weight polymers were visible on the gel. FIGS. 3A, 3B and 3C represent densitometric scans of the product of this invention separated by SDS-polyacrylamide gel electrophoresis using the technique described in the LKB note 306 (LKB Instruments, Gaithersburg, Md.). The scan was obtained from a Helena Quick Scan, R and D (Helena Laboratories, Beaumont, Tex.) at different stages of polymerization.

Figure 10:
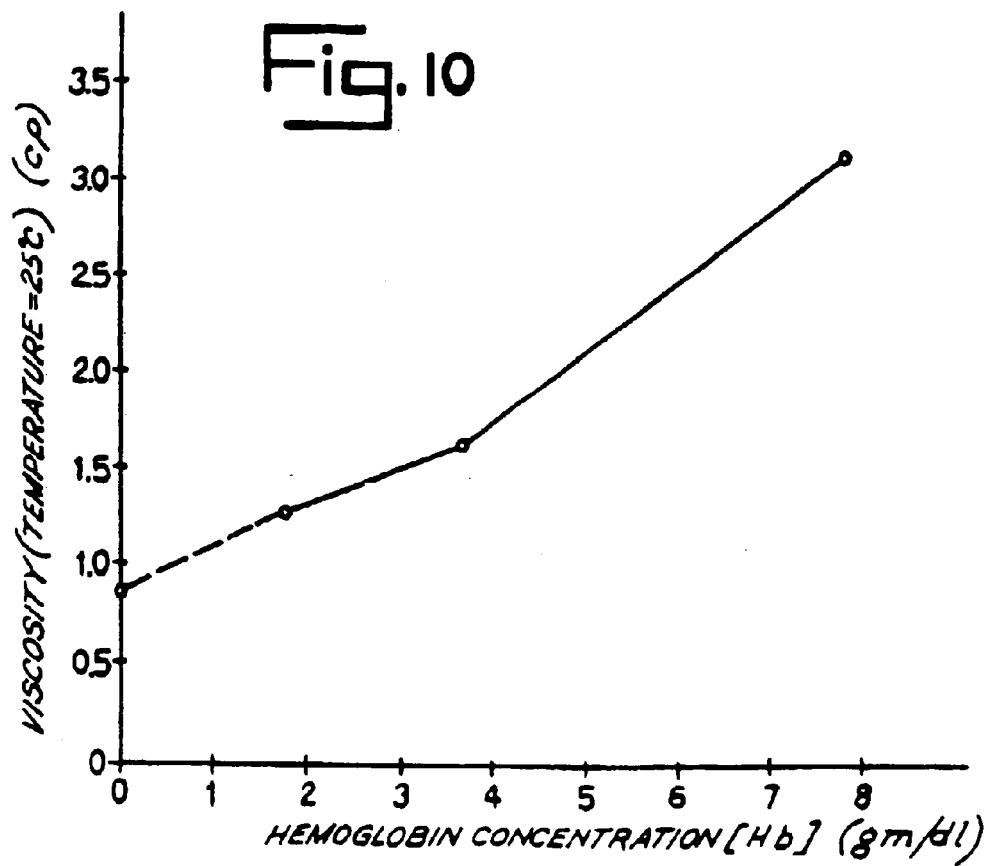
FIG. 10 is a graph describing the relationship between the hemoglobin concentration of the essentially tetramer-free, cross-linked, polymerized, pyridoxylated hemoglobin and the viscosity of the solution.

The viscosity of the product changed with polymerization. The final product had a viscosity of 3.1 centipoise at a hemoglobin concentration of about 8 gm/dl. This value was comparable to that of whole blood. FIG. 10 describes the relationship between the hemoglobin concentration of the product and the viscosity of the solution. The measurements were made with the Brookfield Model LVT viscometer (Brookfield Engineering Laboratories Inc., Stoughton, Mass.) at temperature 25° C. and shear rate 450 $sec^{-1}$.

The phospholipids that were present in the red cell membrane were not detectable in the final product by thin layer chromatography (TLC). Trace amounts of free fatty acids were visible on the TLC plates on an occasional batch.

The methemoglobin reductase activity in the product was essentially unchanged by the process. The starting lysate as well as the final product had enzyme activities ranging from 1.0–2.0 u. One unit of enzyme activity is defined as 1 $\mu$M of ferrocyanide-methemoglobin complex reduced per gram hemoglobin minute.

EXAMPLE 10

Physiological and Biological Assays

A. Renal Alterations

Comparative studies conducted in unanesthetized baboons indicated that infusion of solution contaminated with more than 2–3% tetrameric hemoglobin caused a fall in urine production of approximately 50% and a fall in glomerular filtration rate (creatinine clearance) of approximately 15% as compared to pre-infusion levels. Infusion of pyridoxylated, polymerized hemoglobin solution essentially free of tetramer produced no appreciable effect.

B. Hemodynamic Effects

In baboons a fall of approximately 25% in heart rate and an elevation of approximately 14% in mean arterial pressure was associated with the infusion of a hemoglobin solution contaminated with more than 5–7% tetrameric hemoglobin. This was a primary vasoconstrictor activity of the tetramer and was absent when pyridoxylated, polymerized hemoglobin solution essentially free of tetramer was infused.

C. Extravasation

Up to 2 liters of tetrameric hemoglobin solution was observed in the abdominal cavities of baboons exchange transfused to a hematocrit of 0% with tetrameric hemoglobin. Little if any hemoglobin containing fluid was observed in the peritoneal cavities of animals exchange transfused to a hematocrit of 0% with pyridoxylated, polymerized hemoglobin solution essentially free of tetramer.

D. Destruction of Viral Antigens

A pool of 100 units of human red blood cells, the preferred starting material for the process herein disclosed, tested positive for viral hepatitis B surface antigen. Destruction of this antigen occurred after 1–2 hours of polymerization as described in Example 5.

E. Reduction of Hemoglobin Present in Urine

Infusion of hemoglobin solution containing tetrameric hemoglobin into a baboon resulted in the excretion of tetrameric hemoglobin in urine. This occurred once the mass of infused tetrameric hemoglobin exceeded the baboon's ability to bind hemoglobin tetramer by means of circulating haptoglobin. The resulting urine exhibited a deep red color characteristic of hemoglobin and contained 1–2 gm of hemoglobin per 100 ml of urine. Tetrameric hemoglobin solutions exhibited a 2–4 hour half-life in vivo (mice, baboons were the test animals). Infusion of pyridoxylated, polymerized hemoglobin solution essentially free of tetrameric hemoglobin (less than 2% tetramer present) resulted in little or no appreciable change of the color of the urine (less than 30 mg of hemoglobin per 100 ml of urine). A haptoglobin treated polymerized, pyridoxylated hemoglobin solution (greater than 99.5% free of tetramer) produced no change in the color of the urine, even when infused in very large therapeutic doses in the primate.

Figure 11:
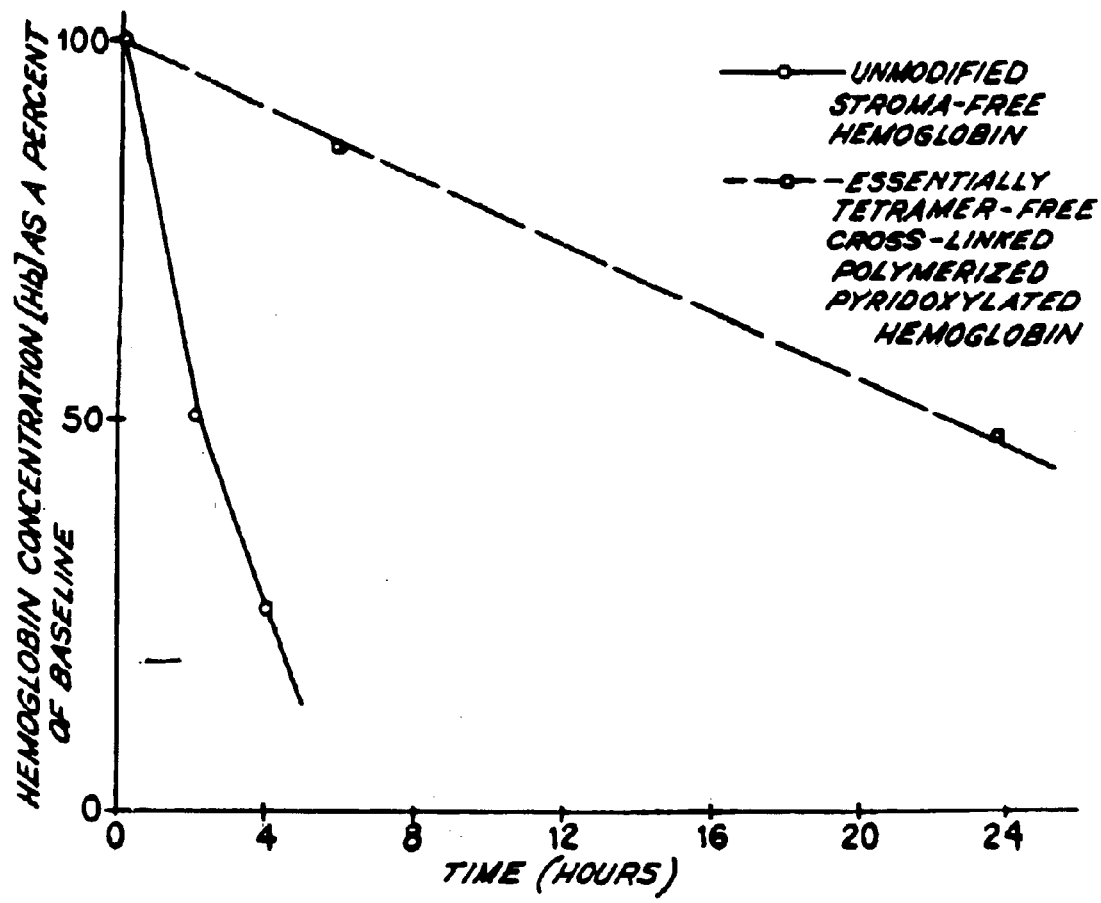
FIG. 11 is a graph describing the plasma disappearance curve for stroma-free hemoglobin (SFH) and essentially tetramer-free, cross-linked, polymerized, pyridoxylated hemoglobin.

The half-life of the product produced by the process herein disclosed was approximately 24 hours (FIG. 11). FIG. 11 describes the plasma disappearance curve (half-life) for the unmodified stroma-free hemoglobin (SFH) and the product of the present invention. One gram per kilogram of body weight of either SFH or essentially tetramer-free, cross-linked, polymerized, pyridoxylated hemoglobin solution in Lactated Ringer's solution, at about 7 to about 14 gm/dl hemoglobin concentration, was administered intravenously to six adult male baboons. Plasma hemoglobin levels were determined by the IL 282, Co-oximeter, at two hour intervals in the case of SPH or at six hour intervals in the case of the product of this invention. The measurements were continued until all hemoglobin disappeared from the test subject's plasma.

In the foregoing, there has been provided a detailed description of preferred embodiments of the present invention for the purpose of illustration and not limitation. It is to be understood that all other modifications, ramifications and equivalents obvious to those having skill in the art based on this disclosure are intended to be within the scope of the invention as claimed.

We claim:

1. Essentially tetramer free, cross linked, polymerized hemoglobin wherein the hemoglobin is from mammalian blood.

2. An aqueous solution of polymerized hemoglobin comprising the polymerized hemoglobin of claim 1.

3. An aqueous solution of polymerized hemoglobin comprising from about 7–18 g/dL of the polymerized hemoglobin of claim 1.

4. An aqueous solution of polymerized hemoglobin according to claim 3, where the solution is essentially tetramer free.

5. An aqueous solution of polymerized hemoglobin according to claim 2, wherein the solution is substantially stroma-free.

6. An aqueous solution of polymerized hemoglobin according to claim 3, wherein the solution is substantially stroma-free.

7. A solution according to claim 6 having an osmolarity of from about 290 mOsM to about 310 mOsM.

8. Cross linked, polymerized hemoglobin wherein the hemoglobin is from mammalian blood and the cross-links are derived from glutaraldehyde.

9. An aqueous solution of polymerized hemoglobin comprising the polymerized hemoglobin of claim 8.

10. An aqueous solution of polymerized hemoglobin according to claim 9, wherein the solution is substantially stroma-free.

11. An aqueous solution according to claim 9, where the solution does not alter renal function.

12. An aqueous solution according to claim 9, where the solution does not cause renal toxicity or hemoglobinurea.

13. An aqueous solution according to claim 9, where the solution contains an amount of tetrameric hemoglobin that does not alter renal function.

* * * * *